(12) United States Patent
Zdeblick

(10) Patent No.: US 11,251,834 B2
(45) Date of Patent: Feb. 15, 2022

(54) SYSTEM FOR SUPPLY CHAIN MANAGEMENT

(71) Applicant: OTSUKA PHARMACEUTICAL CO., LTD., Tokyo (JP)

(72) Inventor: Mark J. Zdeblick, Portola Valley, CA (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/381,313

(22) Filed: Apr. 11, 2019

(65) Prior Publication Data
US 2019/0341967 A1 Nov. 7, 2019

Related U.S. Application Data

(60) Continuation of application No. 15/492,716, filed on Apr. 20, 2017, now Pat. No. 10,305,544, which is a
(Continued)

(51) Int. Cl.
*G06Q 10/06* (2012.01)
*H04B 5/00* (2006.01)
(Continued)

(52) U.S. Cl.
CPC ........... *H04B 5/0012* (2013.01); *A61B 5/061* (2013.01); *G06K 7/01* (2013.01); *G06Q 10/06* (2013.01)

(58) Field of Classification Search
CPC ...... H04B 5/0012; H04B 5/0056; H04B 5/02; A61B 5/061; G06K 7/01; G06K 7/08; G06K 17/00; G06Q 10/06; G06Q 10/08
(Continued)

(56) References Cited

U.S. PATENT DOCUMENTS

| 5,946,550 A | 8/1999 | Papadimitrakopoulos |
| 6,073,050 A | 6/2000 | Griffith |

(Continued)

FOREIGN PATENT DOCUMENTS

| JP | 2010524512 | 7/2010 |
| JP | 2011091680 | 5/2011 |

(Continued)

OTHER PUBLICATIONS

Browne, et al., Let visuals tell the story: Medication adherence in patients with type II diabetes captured by a novel ingestion sensor platform, JMIR Mhealth Uhealth (Dec. 31, 2015), 3(4):e108:1-27.
(Continued)

*Primary Examiner* — Russell S Glass
(74) *Attorney, Agent, or Firm* — Pillsbury Winthrop Shaw Pittman, LLP

(57) ABSTRACT

A system for tracking a product from origin to destination is disclosed. The system includes a probe that comprises two plates, a power source and a processor. The power source is controlled by the processor to produce an oscillating output at the plates. Using the oscillating voltage, the probe interrogates a device through capacitive coupling. The device includes a control unit, a memory unit, and first and second materials physically associated with the device for communication using capacitive coupling. Information associated with the device is transferred from the device to the probe through capacitive coupling between the first and second materials and the first and second plates, respectively.

18 Claims, 9 Drawing Sheets

Related U.S. Application Data division of application No. 14/491,226, filed on Sep. 19, 2014, now Pat. No. 9,941,931, which is a continuation of application No. 13/508,327, filed as application No. PCT/US2010/055522 on Nov. 4, 2010, now Pat. No. 8,868,453.

(60) Provisional application No. 61/258,182, filed on Nov. 4, 2009.

(51) Int. Cl.
 *G06K 7/01* (2006.01)
 *A61B 5/06* (2006.01)

(58) Field of Classification Search
 USPC .......................................................... 600/424
 See application file for complete search history.

(56) References Cited

U.S. PATENT DOCUMENTS

| | | |
|---|---|---|
| 6,946,156 B2 | 9/2005 | Bunick |
| 7,433,731 B2 | 10/2008 | Matsumura et al. |
| 7,449,262 B2 | 11/2008 | Christie et al. |
| 7,527,807 B2 | 5/2009 | Choi et al. |
| 7,811,231 B2 | 10/2010 | Jin et al. |
| 7,871,734 B2 | 1/2011 | Hertz et al. |
| 8,108,083 B2 | 1/2012 | Kameyama |
| 8,709,635 B1 | 4/2014 | Benson et al. |
| 8,785,569 B2 | 7/2014 | Wang et al. |
| 8,801,636 B2 | 8/2014 | Lewicke et al. |
| 9,320,455 B2 | 4/2016 | Hafezi et al. |
| 9,659,423 B2 | 5/2017 | Robertson et al. |
| 10,305,544 B2 * | 5/2019 | Zdeblick .................. G06K 7/01 |
| 10,720,044 B2 | 7/2020 | Zdeblick et al. |
| 10,772,522 B2 | 9/2020 | Zadig |
| 10,797,758 B2 | 10/2020 | Shirvani et al. |
| 2001/0006368 A1 | 7/2001 | Maloney |
| 2003/0040662 A1 | 2/2003 | Keys |
| 2004/0259899 A1 | 12/2004 | Sanghvi et al. |
| 2005/0038680 A1 | 2/2005 | McMahon |
| 2005/0043583 A1 | 2/2005 | Killman et al. |
| 2006/0107997 A1 | 5/2006 | Matsui et al. |
| 2007/0016443 A1 | 1/2007 | Wachman et al. |
| 2007/0025739 A1 | 2/2007 | Moore et al. |
| 2007/0122455 A1 | 5/2007 | Myers et al. |
| 2008/0061945 A1 | 3/2008 | Hoshina |
| 2009/0010321 A1 | 1/2009 | Chalopin et al. |
| 2009/0234203 A1 | 9/2009 | Arita |
| 2010/0019848 A1 | 1/2010 | Rossi |
| 2011/0231202 A1 | 9/2011 | Hanina et al. |
| 2012/0220838 A1 * | 8/2012 | Zdeblick .............. H04B 5/0056 600/302 |
| 2014/0261990 A1 | 9/2014 | Dadey et al. |
| 2018/0279910 A1 | 10/2018 | Jensen et al. |
| 2019/0133958 A1 | 5/2019 | Hafezi et al. |
| 2019/0158151 A1 | 5/2019 | Shirvani et al. |
| 2019/0191006 A1 | 6/2019 | Thompson |

FOREIGN PATENT DOCUMENTS

| | | |
|---|---|---|
| WO | 200016236 | 3/2000 |
| WO | 2004071575 | 8/2004 |
| WO | 2006001001 | 1/2006 |
| WO | 2006057820 | 6/2006 |
| WO | 2015112604 | 7/2015 |
| WO | 2019018762 | 1/2019 |

OTHER PUBLICATIONS

Frias, et al., Effectiveness of Digital Medicines to Improve Clinical Outcomes in Patients with Uncontrolled Hypertension and Type 2 Diabetes: Prospective, Open-Label, Cluster-Randomized Pilot Clinical Trial, J Med Internet Res (2017), 19(7):e246, pp. 1-16.

Guimard et al., Design of a Novel Electrically Conducting Biocompatible Polymer with Degradable Linkages for Biomedical Applications, MRS Proceedings, 950, 0950-D09-08. (Year: 2006).

Kang, et al., Tungsten/copper composite deposits produces by a cold spary, Scripta Materialia (2003), 49:1169-1174.

Martins, et al., Polypyrrole coatings as a treatment for zinc-coated steel surfaces against corrosion, Corrosion Science (Apr. 22, 2004), 46:2361-2381.

Noble et al., Medication adherence and activity patterns underlying uncontrolled hypertension: Assessment and recommendations by practicing pharmacists using digital health care, Journal of the American Pharmacists Association (2016), 56:310-315.

Rivers et al., Synthesis of a Novel, Biodegradable Electrically Conducting Polymer for Biomedical Applications, Adv. Funct. Mater. (Jan. 2002), 12(1):33-37.

Savage, Predictive Analytics: Advancing Precision and Population Medicine, Harvard Health Policy Review (2015), 14(2):1-4.

Van der Biest, et al., Electrophoretic Deposition of Materials, Annu. Rev. Mater. Sci. (1999), 29: pp. 327-352.

* cited by examiner

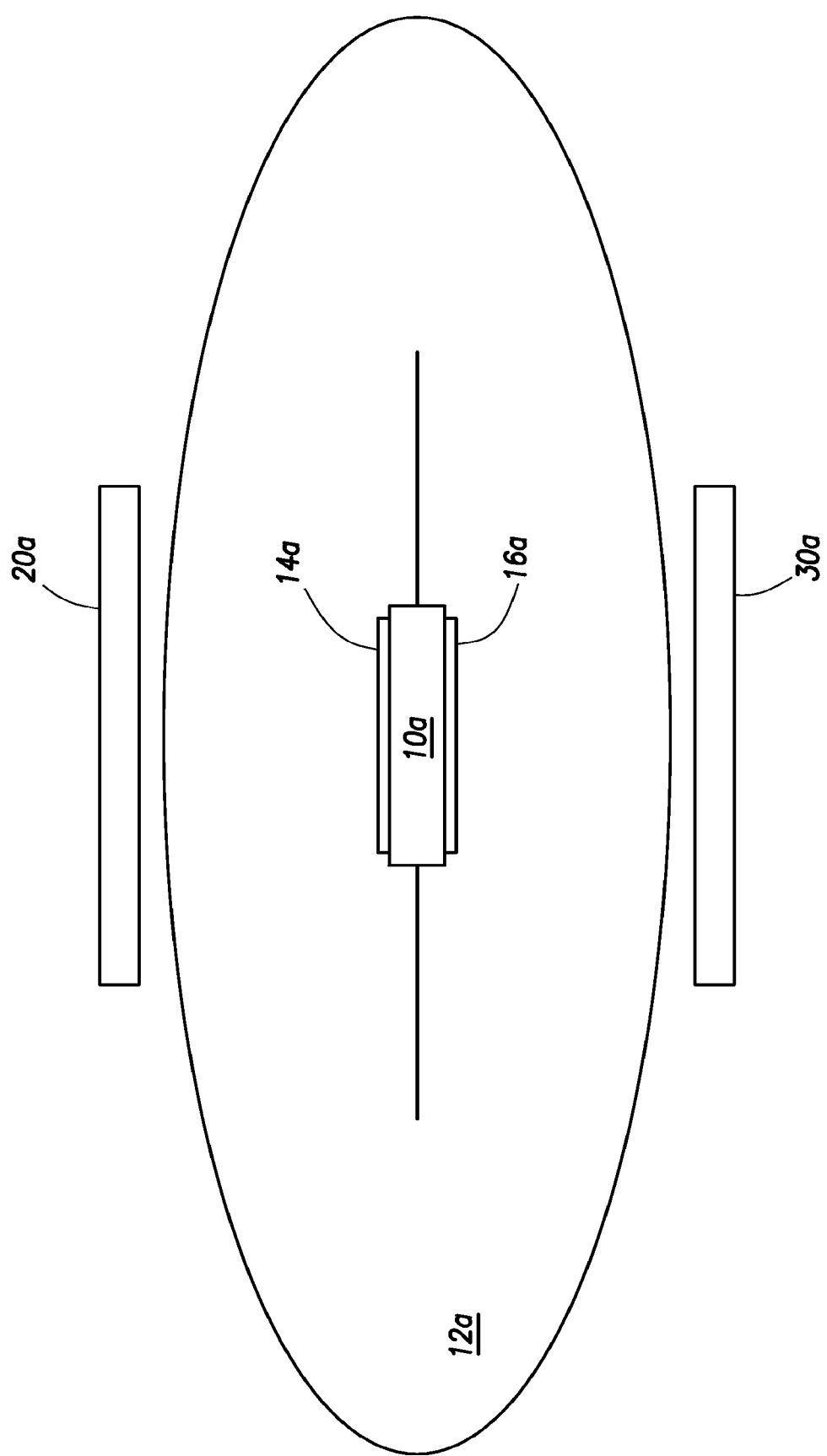

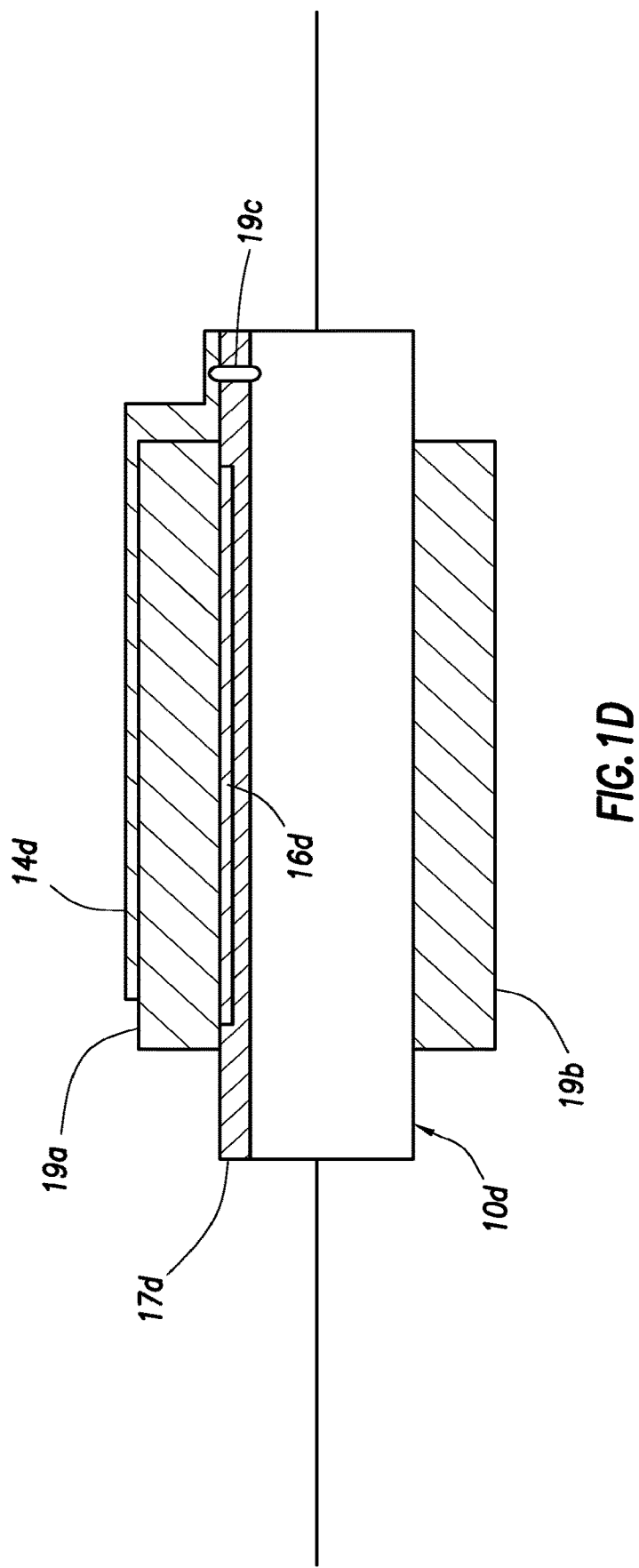

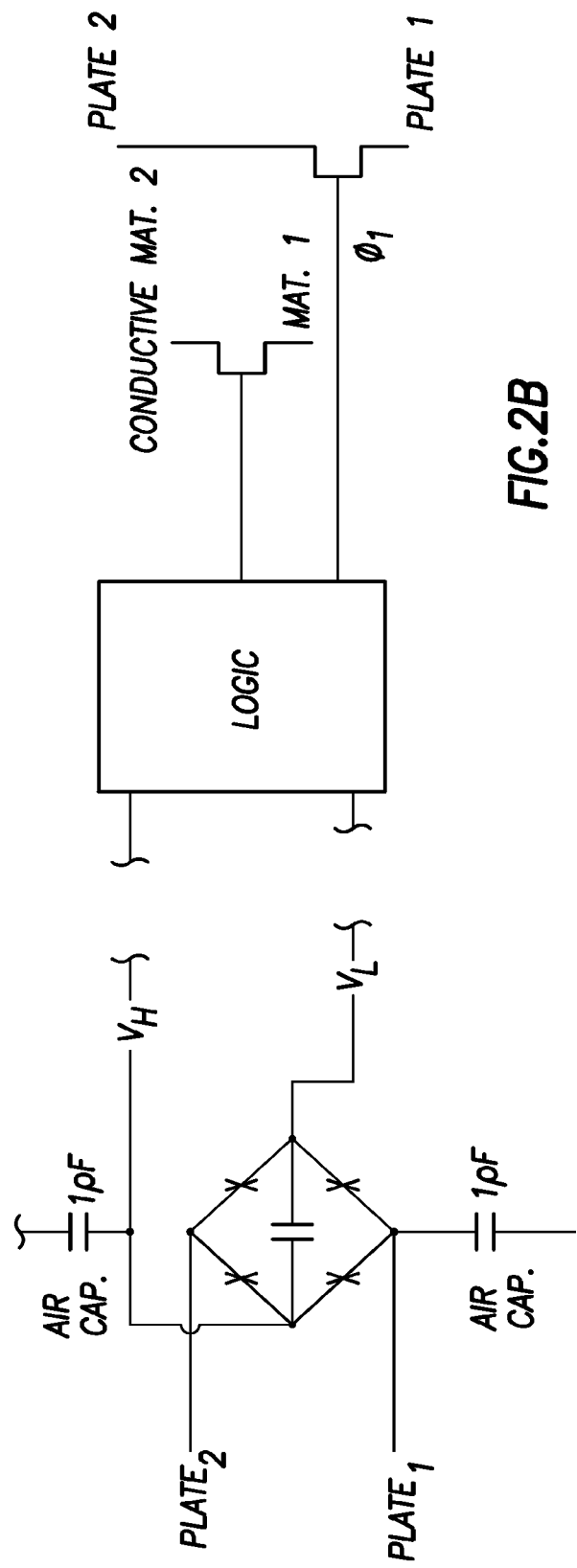

SYSTEM FOR SUPPLY CHAIN MANAGEMENT

CROSS-REFERENCE TO RELATED APPLICATIONS

This application claims priority under 35 USC 119 from U.S. Provisional Application Ser. No. 61/258,182 filed on Nov. 4, 2009 titled Method, Device and System for Supply Chain management of Ingestible Event Markers by inventor Mark Zdeblick, which is incorporated herein.

FIELD OF THE INVENTION

The present invention is related to methods and systems for using electronic devices to track products. More specifically, the present disclosure includes a methods, devices, and system for tracking medical inventory from source to consumer.

BACKGROUND

Suppliers of pharmaceutical products are concerned about counterfeit products being substituted for original products from the time the products leave the manufacturer to the time the products are delivered to the end user. Additionally, there is a need for accurately determining the quantity and content of a package so that the distributors can identify the products throughout the supply chain. Known methods and systems use near field communication, such as RFID. These known methods have inherent limitations such as lack of data integrity, confidentiality etc. Therefore, what is needed is a system for interrogating a product to ensure validity and origin of the product throughout the supply chain, from manufacturer to end user or consumer.

SUMMARY

Disclosed is a system to manage product supply in a supply chain environment. In various aspects, the invention includes capacitive plates which probe a variety of products, resulting in indications of product validity or invalidity. In this manner, various supply chain or other pursuits may be accomplished.

The products include, for example, IV bags, syringes, ingestible event markers (IEMs) and similar devices, as disclosed and described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753 published as WO 2009/042812; PCT application serial no. PCT/US09/53721; and PCT application serial no. PCT/US2007/015547 published as WO 2008/008281; as well as U.S. Provisional Application Ser. Nos. 61/142,849; 61/142,861; 61/177,611; 61/173,564; each in its entirety is incorporated herein by reference. Such products may typically be designed to include conductive materials/components. The use of capacitive coupling to probe the product's conductive materials and components by the capacitive plates may indicate the presence of the correct configuration of conductive components of the product. Alternatively, failure to communicatively couple when probed may indicate product nonconformance, e.g., one or more conductive materials is absent, incorrectly configured, etc.

BRIEF DESCRIPTION OF THE DRAWINGS

FIG. 1A shows a pharmaceutical product with a device that can be interrogated using capacitive coupling in accordance with one aspect of the present invention.

FIG. 1D shows a device that can be probed or interrogated using capacitive coupling in accordance with yet another aspect of the present invention.

FIG. 2A shows a diode bridge use in the device of FIG. 2.

FIG. 2B shows a logic unit of the device of FIG. 2 in communication with a probe through the plates and the conduction material, which is associated with the device in accordance with the present invention.

DETAILED DESCRIPTION

Figure 1B:
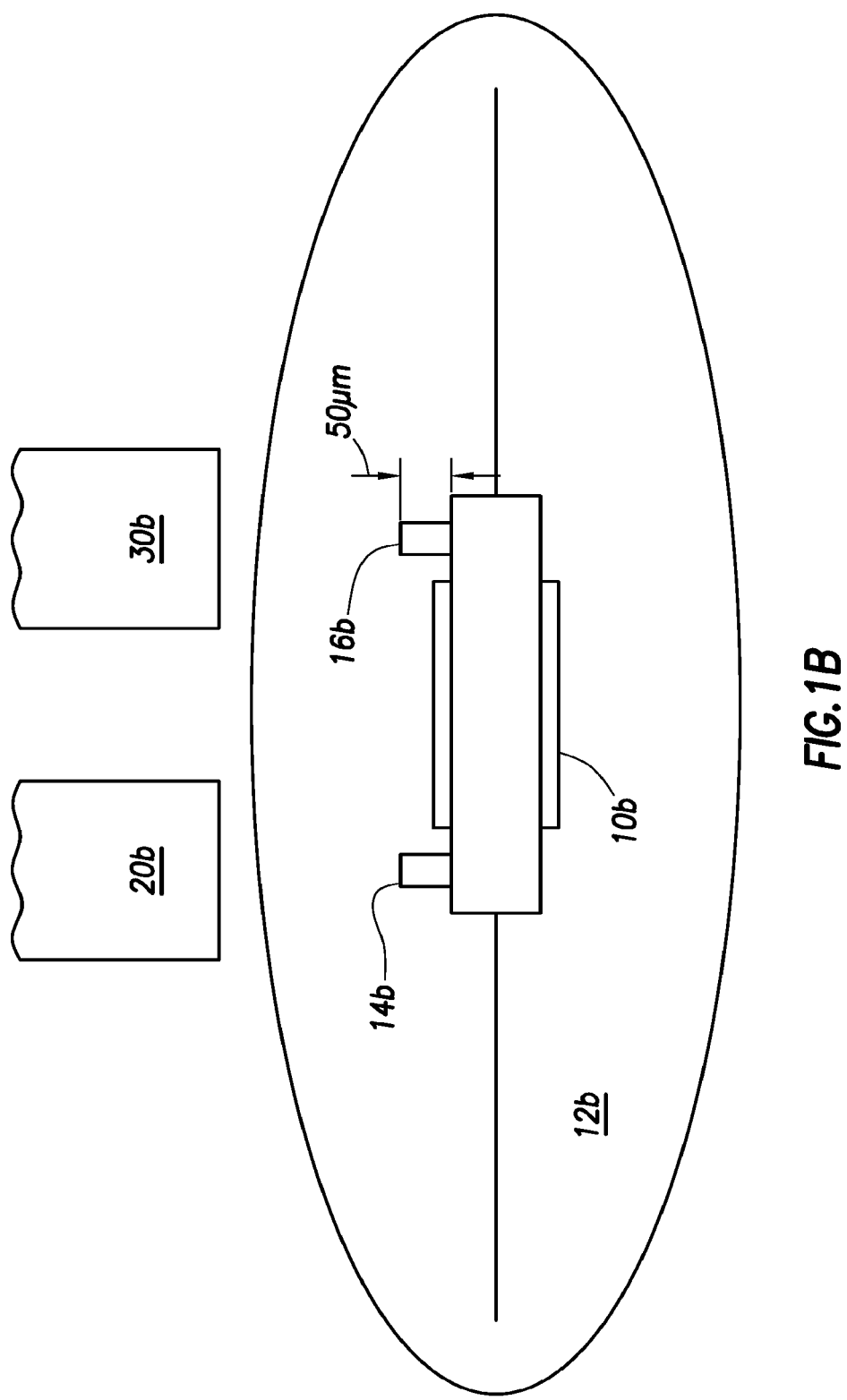
FIG. 1B shows a pharmaceutical product with a device that can be interrogated using capacitive coupling in accordance with another aspect of the present invention.

Referring now to FIG. 1A, a device 10a inside a pharmaceutical product 12a, such as a pill or tablet, which is completely packaged up and tested via a probe, as discussed in detail below. In accordance with various aspects of the present invention, the device 10a may be located within the product 12a or secured to the surface of the product 12a, as contemplated within the scope of the present invention. The device 10a includes a control module for communication and a memory for storing information, such as identity. The probing of the device 10a is performed to ensure, for example, that the device 10a is still functioning. The probing uses a capacitive coupling approach where there is capacitive coupling of a first probing capacitive plate 20a to a first metal or material 14a on one side of the device 10a and a second probing capacitive plate 30a to a second metal or material 16a on another side of the device 10a. As evident to one skilled in the art, the plate 20a is electrically insulated from the plate 30a even though the insulation is not specifically shown. Various ways to probe using capacitive coupling may be accomplished, e.g., metal, metal pads, etc. In accordance with one aspect of the present invention, for example, there is capacitive coupling between material 14a and capacitive plate 20a and material 16a and capacitive plate 30a. The plates 20a and 30a are probes that can communicate with the device 10a through capacitive coupling. The plates 20a and 30a are electrically connected to a system (not shown) that can receive the information from the plates 20a and 30a as well as process the information. Also, in accordance with various aspects of the present invention, the product may be coated with non-conducting material.

In accordance with various aspects of the present invention, there are various components included as part of the device 10. For example, the device 10 may be an ingestible event marker (IEM) with a unique identity that can be read using capacitive coupling pre-ingenstion and communicated using transconduction post-consumption. Various aspects of an IEM are disclosed in U.S. patent application Ser. No. 12/564,017 titled COMMUNICATION SYSTEM WITH PARTIAL POWER SOURCE filed on Sep. 21, 2009, the entire disclosure of which is incorporated herein by reference.

Referring now to FIG. 1B, a device 10b is shown as part of a product 12b in accordance with one aspect of the present invention. The device 10b includes a first material 14b and a second material 16b deposited on the surface of the device 10b for forming a capacitive connection. The materials 14b and 16b are in communication with the control module of the device 10b. Probes 20b and 30b are capacitively coupled to materials 14b and 16b, respectively. Thus, as the probes 20b and 30b are powered up with AC voltage, then materials 14b and 16b are capacitively coupled to the probes 20b and 30b. Thus, information associated with the device 10b that is stored in the memory of the device 10b can be encoded by a control module of the device 10b and communicated to the probes using capacitive coupling.

Figure 1C:
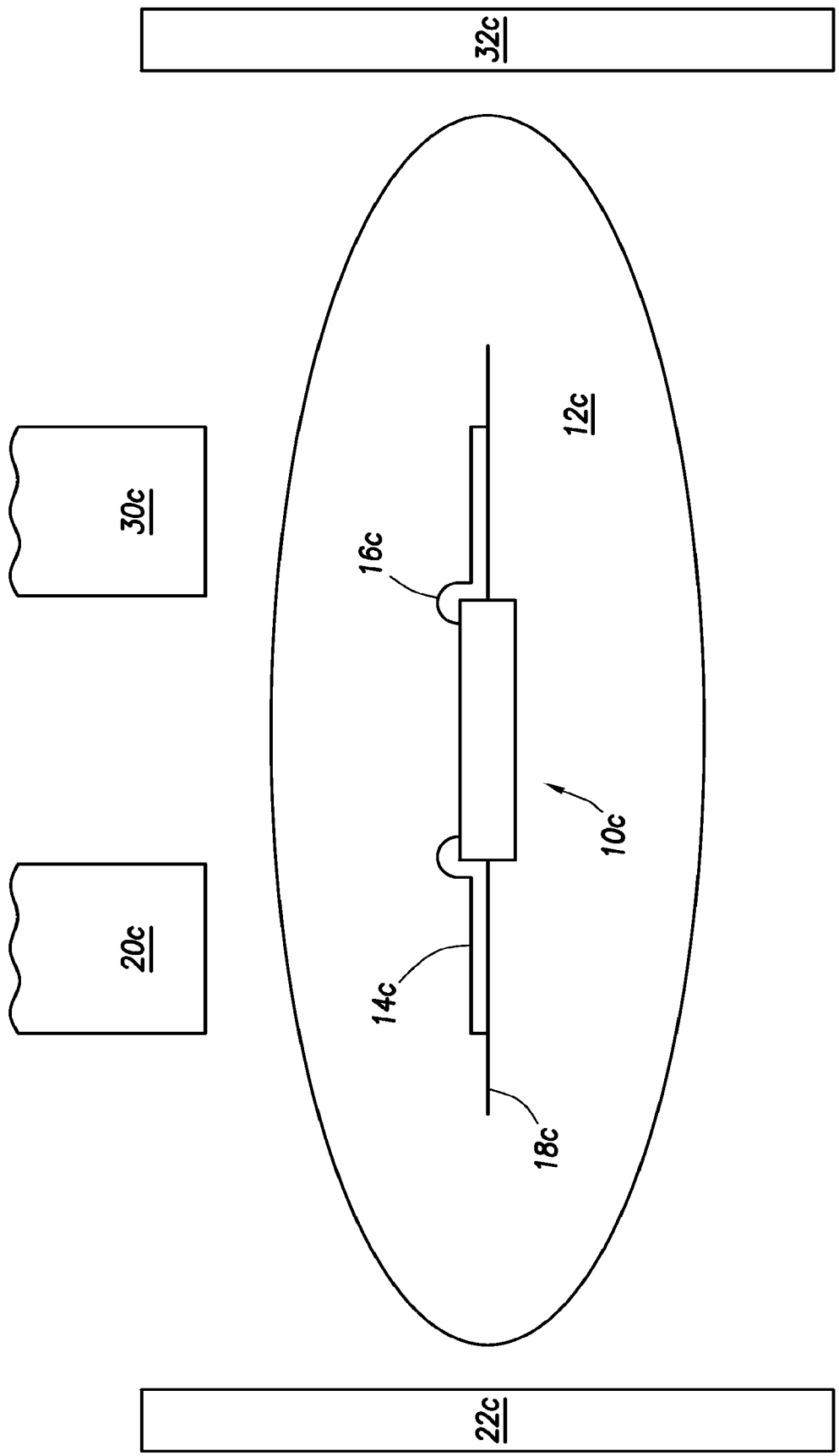
FIG. 1C shows a pharmaceutical product with a device that can be interrogated using capacitive coupling in accordance with another aspect of the present invention.

Referring now to FIG. 1C, a device 10c is shown secured to a product 12c in accordance with the present invention. The device 10c includes a first material 14c and a second material 16c deposited around the perimeter of a skirt 18c of the device 10c with at least a portion of the materials 14c and 16c being deposited on the skirt 18c. Furthermore, the materials 14c and 16c are coupled to the control module of the device 10c to allow for communication through capacitive coupling from the control module of the device 10c to allow the identity of the device 10c to be communicated to a system through the probes 20c and 30c. In accordance with one aspect of the present invention, the materials 14c and 16c are conductive inks, such as an ingestible graphite or carbon based ink or paste. Probes 20c and 30c are powered by an AC source and when brought close to the materials 14c and 16c, the probes 20c and 30c can communicate with the device 10c using capacitive coupling through the materials 14c and 16c, respectively. Furthermore, in accordance with another aspect of the present invention, probes 22c and 32c are positioned proximal to the material 14c and 16c at different locations to allow for alternative positioning of the device 10c or to provide for probing of the device from an alternative direction. Once the probes 20c and 30c are powered with an AC voltage and the device 10c is located near the probes 20c and 30c, then the materials 14c and 16c can be used to pass information between the device 10c and the system connected to the probes 20c and 30c through capacitive coupling.

Figure 2C:
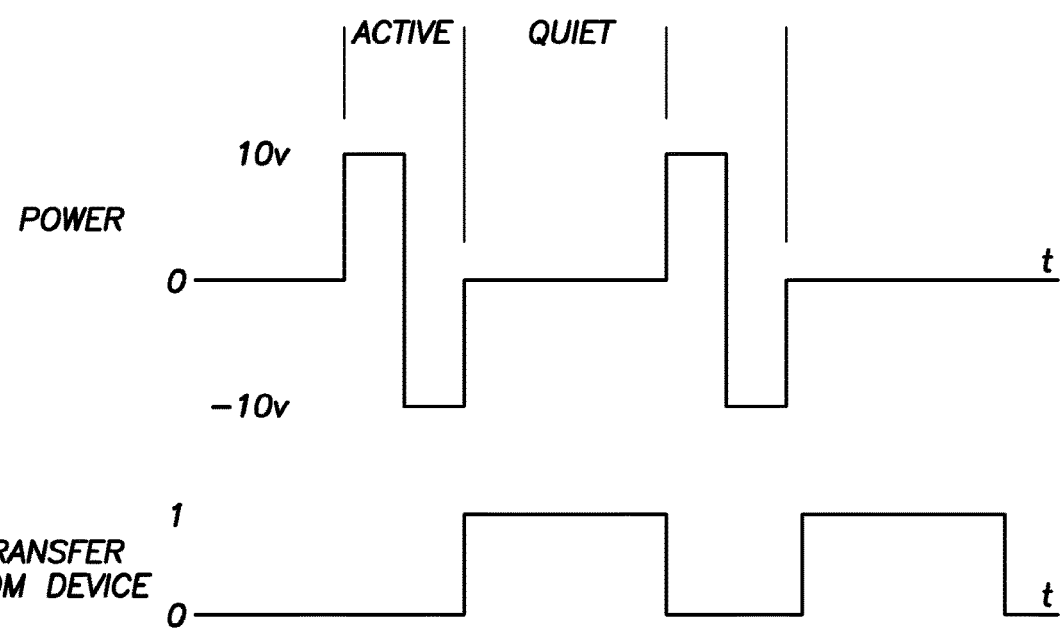
FIG. 2C shows a finite time period for a power transfer cycle and an information transfer cycle using capacitive coupling in accordance with the teachings of the present invention.

Referring now to FIG. 1D, a device 10d is shown in accordance with another aspect of the present invention. A conducting material 14d is deposited on the surface of a material 19a that is associated with the device 10d. The material 19a and the material 19b of the device 10d are dissimilar materials and form a partial power source for the device 10d. For example, the material 19a maybe CuCl and the material 19b may be Mg. The device 10d also includes transistors at connection 19c that is capable of electrically connected the composite 14d to V-high or the material 19b, which is at the same potential as V-low. The device 10d includes a composite material 16d that is physically associated with the device 10d and rests on top of an oxide layer 17d. The material 16d may be gold-plated CuCl. Thus, as probes or plates, similar to those shown in FIGS. 1A-1C and powered by an oscillating or AC voltage source, are brought close to the device 10d there is capacitive coupling between the composite 14d and the composite 16d and the probes. In accordance with one aspect of the present invention, as the voltage source isolates, the energy transferred to the material 14d and the material 16d varies accordingly and is stored on the device 10d. As the voltage source is reduce to zero or quiet, then the device 10d switches from receiving energy to sending energy to the probes using capacitive coupling. In order to creating an oscillating energy source, the transistors 19c are used to connect and disconnect the material 14d between the material 19b (which represents V-low) and V-high. As the material 14d changes energy levels from V-high to V-low, information can be transferred to the probes. Thus, during a portion of the cycle when the power is off or quiet (as shown in FIG. 2C), the device 10d is able to transfer energy to the probes, which energy includes information about the device 10d. Hence, using capacitive coupling, information may be communicated between the device 10d and the system connected to the probes near the device 10d.

Figure 1E:
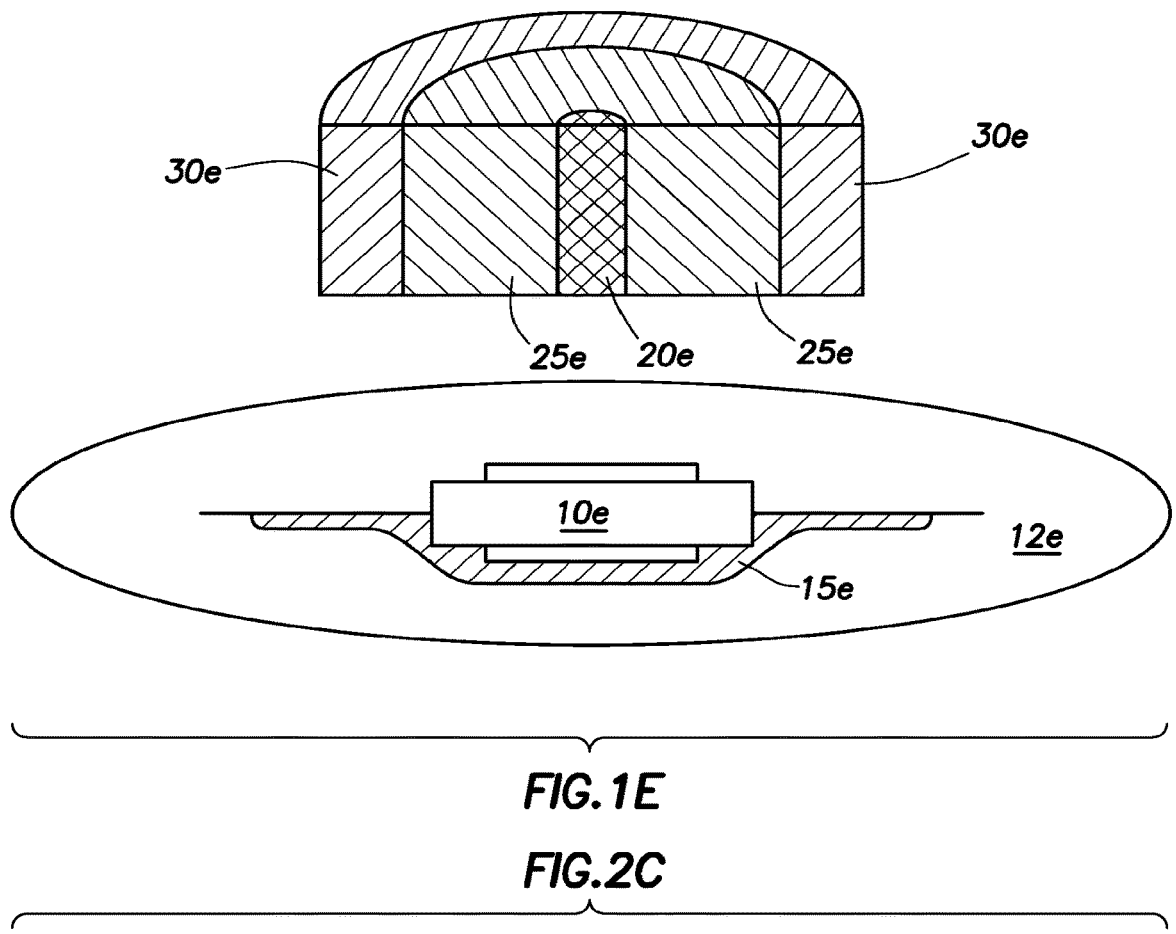
FIG. 1E shows a pharmaceutical product with a device that can be probed or interrogated with a co-axial probe/plates using capacitive coupling in accordance with yet another aspect of the present invention.

Referring now to FIG. 1E, a co-axial probe with two conductive probes/plates 20e and 30e separated by an insulating material 25e. The inner conductive probe or plate 20e is surrounded by the insulating material 25e, which is surrounded by the outer conductive probe or plate 30e. The device 10e is shown as part of a pharmaceutical product 12e. The device 10e includes a conducting material or ink 15e deposited on the side opposite the co-axial probe. As the co-axial probe is positioned close to the product 12e, the probe 20e is positioned over the center of the device 10e and the probe 30e is positioned above the outer edges of the device 10e and proximal to the material 15e. Thus, as described above and with respect to FIG. 2C, as the power source is isolating, energy is transferred from the co-axial probe to the device We and as the power source is shut-off or quiet, then energy is transferred from the device 10e to the system connected to the co-axial probe.

Figure 2:
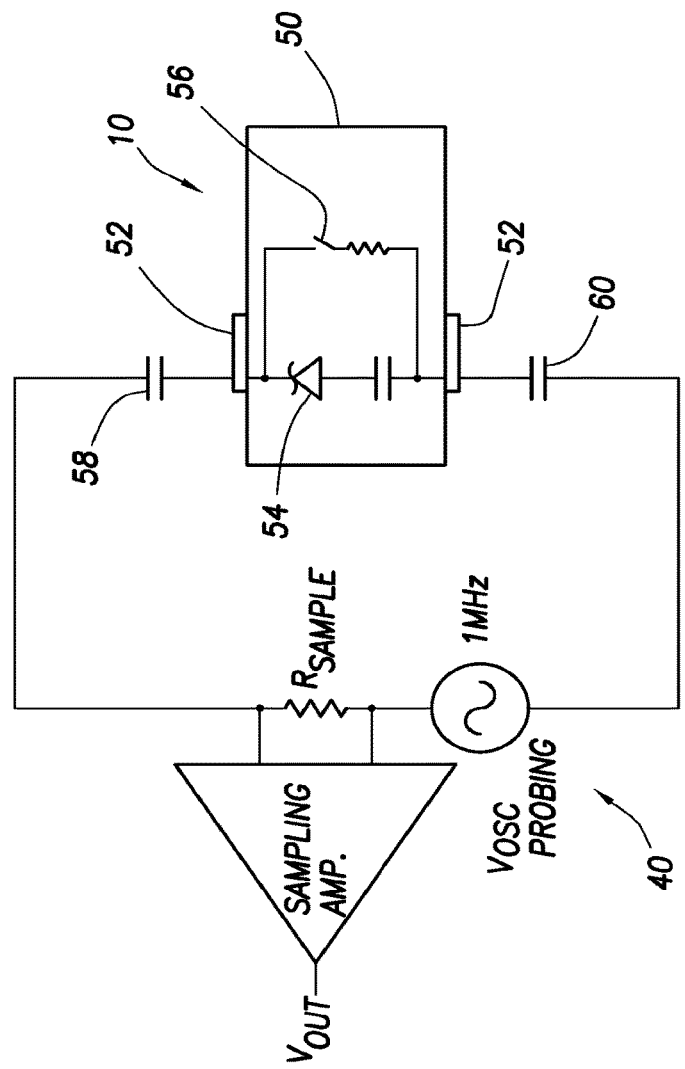
FIG. 2 shows a circuit diagram for the device of FIGS. 1A-1D in accordance with one aspect of the present invention.

Referring now to FIG. 2, a voltage source, e.g., an AC voltage or other isolating or alternating source 40 runs at a high frequency, e.g., 1 MHz, etc. The voltage source is connected to the probes or plates. The device 10 includes a control module 50 and bonding pads 52 to which the materials (for example, materials 14 and 16 of FIG. 1A) are coupled. In accordance with one aspect of the present invention, inside the device 10 is a diode 54, such as a Schottky diode or other type of diode that creates an internal supply voltage, and a switch 56 with some impedance that is turned on and off which changes the impedance of the device 10. The variation in the impedance is used to communicate information about the identity of the device 10. The change in impedance allows for the information associated with the device 10 to be encoded and sent to a system through the probes using capacity coupling, as represented by the capacitors 58 and 60. The information is captured by the system connected to the probes represented by the capacitors and read as Vout through the sampling amplifier across the impedance labeled R-sample.

Once the control module 50 is brought near or exposed to the voltage source through the plates, there is energy transfer through the capacitive coupling and the device 10 can produce an oscillation signal, which can be detected. The oscillation signal contains information and the isolating signal can be encoded into, for example, a 1 MHz signal or similar frequency, e.g., 500 KHz, as may be dependent on the degree of capacitive coupling. The voltage of the source 40 will be determined by how much capacitive coupling is achieved between the capacitive plate or probe 20 and 30 of FIG. 1 and the materials 14 and 16 thereof. Thus, at a high frequency that represents, perhaps, 5 volts, the capacitive value between the probe, such as probe 20 or 30, and the material is represented by the capacitors 58 and 60.

Referring now to FIGS. 2A and 2B, in accordance with another aspect of the present invention, a diode bridge is shown that is a circuit representation of the interaction between the plates 20 and 30 and the materials 14 and 16 of the device 10. The isolating voltage present at the plates 20 and 30 (labeled "PLATE 1" and "PLATE 2") results in an energy transfer in the form of high voltage and a low voltage for the device 10. The device 10 includes a control module as part of the processor or logic unit. The logic unit may be a processor, a microprocessor, a multi-module device or any form of integrated circuit. The logic unit is in communication with the conductive materials 14 and 16 and the plates 20 and 30 (labeled "PLATE 1" and "PLATE 2"). As the plates 20 and 30 are powered with an AC source, the logic unit stores energy and later uses that energy to send information.

Referring now to FIG. 2C, the power cycle is shown with an active period and a quiet period and the transfer cycle of the device 10 is shown as the transfer window. In accordance with the present invention, the duration of the active period energy is transferred from the power source to the device 10. Then during the quiet phase, the energy stored by the device 10 is used to transfer energy from the device 10 to the system connected to the probes. In this way, information associated with the device can be transferred from the device 10 through the probes 20 and 30 to the system connected to the probes. In accordance with various aspects of the present invention, the information sent from the device 10 to the system of the probes 20 and 30 during the quiet phase is based on the information stored in memory of the device. Thus, even though there is a "1" shown during the transfer window or quiet stage of the power source, the information transferred during the quiet stage or phase of the power source may be a "0".

In accordance with one aspect of the present invention, if there is a one-microfarad capacitor between a capacitive plate/probe and a material physically associated with the device 10, then at a high isolating frequency that represents a lower voltage necessary for capacitive coupling. In accordance with another aspect of the present invention, if there is a one-picofarad capacitor, then a larger voltage may be needed, as will be recognized by one skilled in the art. The amount of current actually going through will depend on the impedance between the electrical circuit caused between the capacitive plates/probes 20 and 30, as shown in FIG. 1 for example. Thus shorting capacitive plate 20 and capacitive plate 30 of FIGS. 1A-1C will result in significant current going through which may be detected with, for example, by a sampling amplifier as shown in FIG. 2. The output is through a sampling amplifier which is essentially looking at the current going through the loop and the modulation of that current caused by the control module 50.

In accordance to various aspects of the present invention, the capacitive coupling may be used with devices that are DC source devices, which are modified for interoperability, e.g., a device having a rectifier in place to provide a stable voltage on the chip, the impedance of which may be modulated.

Figure 3A:
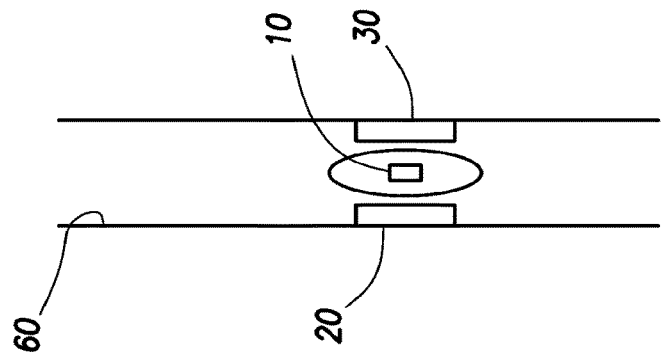
FIG. 3A shows a product with the device passing through a tubular section to confirm product authenticity and device operation in accordance with the present invention.
Figure 3B:
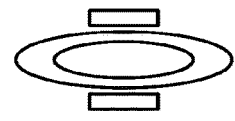
FIG. 3B is a specific instant of the device passing between plates during interrogation to confirm authenticity of the product in accordance with the present invention.

Referring now to FIGS. 3A and 3B, in accordance with various aspects of the present invention, the capacitive plates/probes and the system connected thereto for receiving information may be integrated or otherwise associated with various structural components and other devices, e.g., a tubular structure 60 as shown in FIG. 3A having capacitive plates 20 and 30. To illustrate, one or more pharmaceuticals having an IEM or similar device 10 may be introduced into the structure. The device 10 may be introduced manually or automatically via automated means. As the device travels through the structure 60, the device 10 is probed by the capacitive plates 20 and 30 in the tube 60. In various aspects, other devices and/or components may be associated. In one example, a programmable device may be communicatively associated with the capacitive coupling device to receive and/or transmit data and/or information derived by the capacitive coupling device. To continue with the foregoing illustration, once all or a portion of the number of products 10, which may be pills, are probed or "read" by the capacitive coupling system associated with the probes/plates 20 and 30, the capacitive coupling system can communicate, e.g., wireless, wired, etc., to a database with a display device for further storage, display, manipulation, etc. In this manner, an individual datum, data, large volumes of data, etc., may be processed for various purposes. One such purpose may be, for example, to track pharmaceuticals in a supply chain application, e.g., during a manufacturing process such as a tablet pressing or other process, during a pharmacy verification process, during a pharmacy prescription process, etc. Various processes may be complementary, incorporated, etc. One such example is validation through reading the number. If it is valid, e.g., readable, the tablet is accepted. If not, the tablet is rejected. Thus, using a simple hand held reader with an oscillating power source, a user or care provider can probe the product, which can be a pill or tablet in accordance with one aspect of the present invention, with the device 10 associated therewith and determine if the pill is authentic or a counterfeit product.

Figures 4A, 4B:
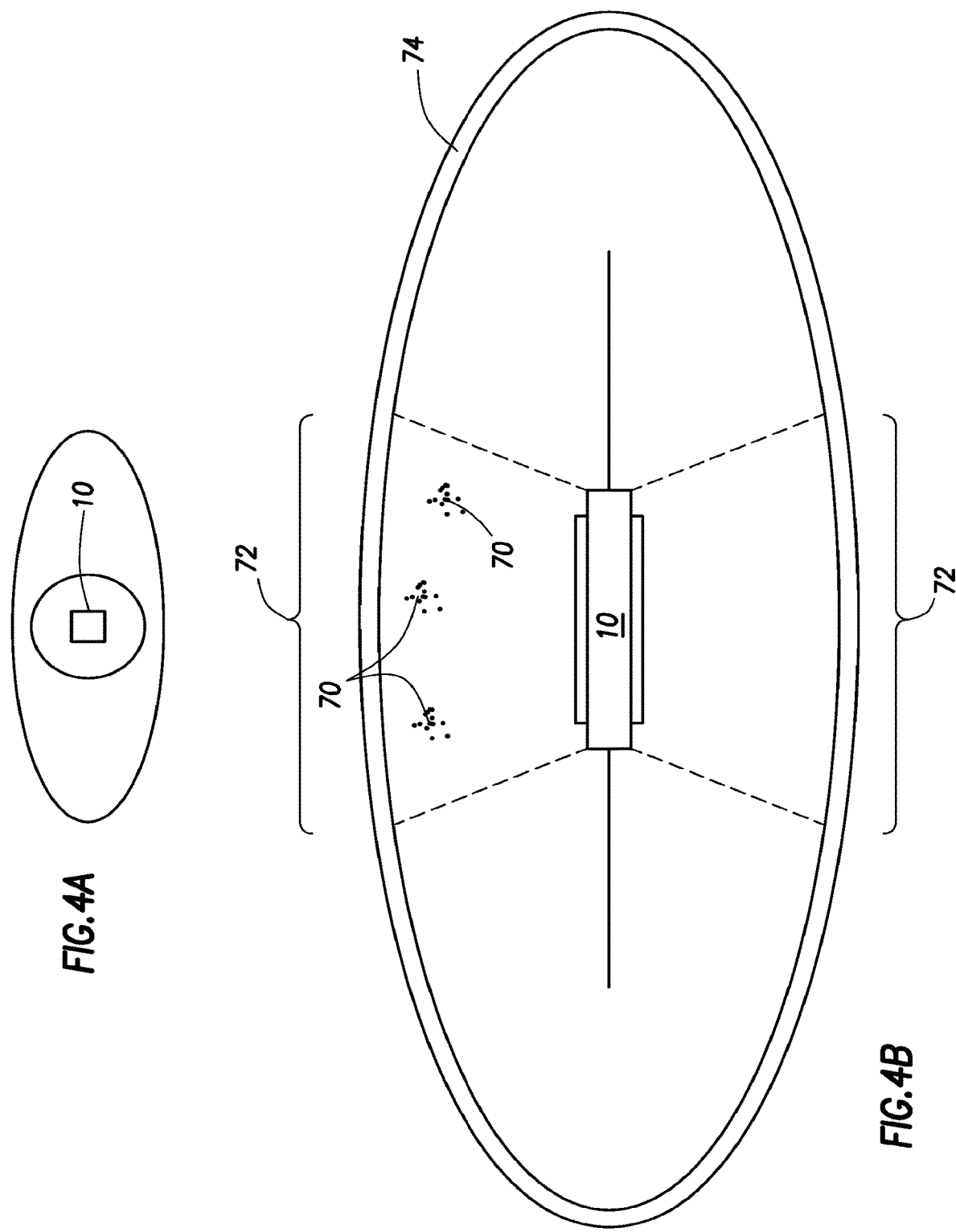
FIG. 4A is a top view of the device associated with a product in accordance with the present invention.
FIG. 4B is a side view of a product with a conducting composite and the device in accordance with the present invention.

Referring now to FIGS. 4A and 4B, in accordance with another aspect of the present invention, a pill having a device 10 is shown with a coating 74 that is non-conductive or fairly impervious coating and the pill itself comprises a non-conductive medicine powder. A region 72, e.g., a cone-shaped region, as shown, comprises a conductive material 70, e.g., small particles or grains of conductive material intermixed with other pharmaceutical material(s), excipient(s), placebo material(s), etc., such that the region 72 is converted into a conductive region. For example, graphite and other conductive materials may be used, e.g., one part in ten, five parts in ten, etc. such that the region 72 is conductive. Other materials and compositions are possible, e.g., a gel or liquid capsule having conductive particles therein, etc. Thus, at high enough frequencies, the particles of the conductive material 70 in the region 72 may be shorted together. One skilled in the art will recognize that the conductive material 70 may include various materials and form factors, as well as combinations thereof, e.g., variously sized particles, wires, metal films, threads, etc. The scope of the present invention is not limited by the type or shape of the conductive material 70 used in the region 72.

In accordance with another aspect of the present invention, the conductive material 70 may be integrated or formed via a variety of methods and proportions. In one example, the device 10 is embedded or otherwise mechanically associated with a "doughnut-shaped" powder and the hole formed therein is filled or otherwise associated with the conductive particles, etc., to form the conductive region. The size, area, volume, locations or other parameters of the conductive regions may vary to the extent the functionality described herein may be carried out.

Figure 5:
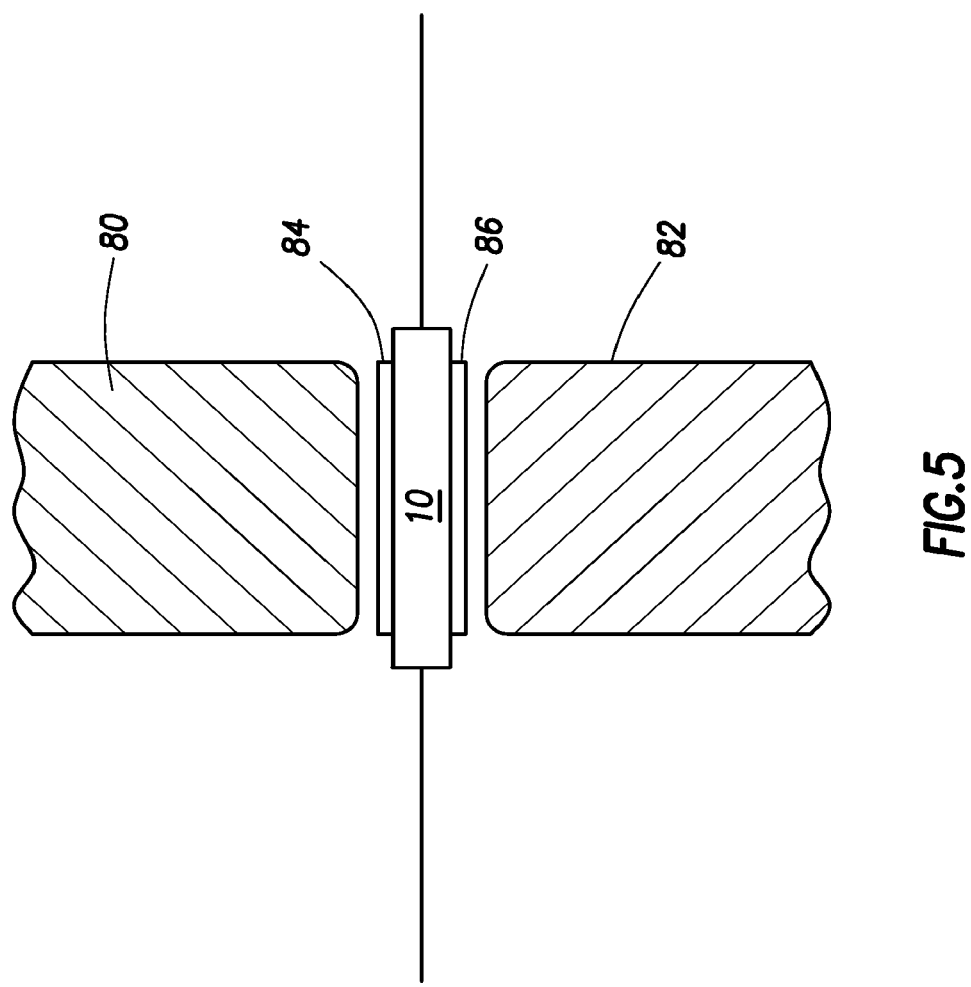
FIG. 5 shows a side view of a device being interrogated by a pair of probes in accordance with the present invention.

In accordance with another aspect of the present invention and as shown in FIG. 5, capacitive plates or probes 80 and 82 are coupled to a system for collecting the data. Probes 80 and 82 are used to probe the device 10 through capacitive coupling to the materials 84 and 86, respectively. An impedance feedback system may be used to drive them fairly close to one another and once the current gets to a certain amount to use that to gauge the distance. Using a high enough impedance, this system may be useful in a variety of applications, e.g., a manufacturing environment to validate that the device 10 is present, is operating correctly etc.

In accordance with another aspect of the present invention, a close proximity between the capacitive coupling probes/plates and the device 10 may facilitate, promote, etc., privacy aspects. In certain aspects, certain related devices may include, for example, a circuit with a Schottky diode in parallel with a CMOS transistor that is timed to be opened and closed, opened up, etc. Other circuit designs and modifications are possible.

What is claimed is:

1. A system for tracking an ingestible device and detecting a counterfeit as the ingestible device travels from origin to destination, the system comprising:
    an interrogation unit comprising:
        a power source configured to produce an oscillating voltage;
        a processor coupled to the power source and configured to receive and send information and control the output of the power source;
        a first plate coupled to the processor and configured to be communicably coupled to a first capacitive element of the ingestible device; and
        a second plate coupled to the processor and configured to be communicably coupled to a second capacitive element of the ingestible device;
    wherein the power source is controlled by the processor to produce the oscillating voltage at the first plate and the second plate;
    wherein the first and second plates are configured together to power on the ingestible device by transferring energy to the first and second capacitive elements, respectively, using the oscillating voltage; and
    wherein the processor is further configured to receive information from the ingestible device through the first and second plates by measuring a variation in impedance level of the ingestible device.

2. The system of claim 1, wherein the interrogation unit is configured to identify the ingestible device using the information received from the ingestible device.

3. The system of claim 1, wherein the information is transferred from the ingestible device to the interrogation unit through capacitive coupling between the first and second capacitive elements and the first and second plates, respectively.

4. The system of claim 1, wherein the first and second plates are facing each other and define a gap of separation distance such that the ingestible device is in communication with the interrogation unit when the ingestible device is positioned between the first plate and the second plates in the defined gap.

5. The system of claim 1, wherein the first and second plates are located in the same plane and positioned side-by-side such that the ingestible device is in communication with the interrogation unit when the ingestible device or a product containing the ingestible device is brought close to the first and second plates of the interrogation unit.

6. The system of claim 1, wherein the interrogation unit is used in part of a manufacturing process of the ingestible device and wherein the interrogation unit is further configured to confirm that the ingestible device is functional through establishing a capacitive coupled communication session that confirms that the ingestible device is operational.

7. The system of claim 1, wherein the processor is further configured to determine that the ingestible device is a counterfeit based on the received information upon interrogating the ingestible device.

8. The system of claim 1, wherein the interrogation unit comprises a co-axial structure, wherein the first plate is an inner plate, the second plate is an outer annular plate, and the inner plate is positioned inside the outer annular plate to form a co-axial formation.

9. The system of claim 1, wherein the interrogation unit comprises a tubular structure, wherein the first and second plates are secured on an inner surface of the tubular structure, and wherein the tubular structure is configured to allow the ingestible device to pass through inside the tubular structure.

10. A method of an interrogation unit for tracking an ingestible device and detecting a counterfeit as the ingestible device travels from origin to destination, the method comprising:
    generating an oscillating voltage by a power source of the interrogation unit;
    powering on the ingestible device by transferring energy, via first and second plates of the interrogation unit communicatively coupled to the ingestible device, to first and second capacitive elements of the ingestible device using the oscillating voltage; and
    receiving information from the ingestible device through the first and second plates by measuring a variation in impedance level of the ingestible device.

11. The method of claim 10, further comprising identifying the ingestible device using the information received from the ingestible device.

12. The method of claim 10, further comprising transferring the information from the ingestible device to the interrogation unit through capacitive coupling between the first and second capacitive elements and the first and second plates, respectively.

13. The method of claim 10, wherein the first and second plates are facing each other and define a gap of separation distance such that the ingestible device is in communication with the interrogation unit when the ingestible device is positioned between the first plate and the second plates in the defined gap.

14. The method of claim 10, wherein the first and second plates are located in the same plane and positioned side-by-side such that the ingestible device is in communication with the interrogation unit when the ingestible device or a product containing the ingestible device is brought close to the first and second plates of the interrogation unit.

15. The method of claim 10, further comprising confirming that the ingestible device is functional through establishing a capacitive coupled communication session that confirms that the ingestible device is operational.

16. The method of claim 10, further comprising determining that the ingestible device is a counterfeit based on the received information upon interrogating the ingestible device.

17. The method of claim 10, wherein the interrogation unit comprises a co-axial structure, wherein the first plate is an inner plate, the second plate is an outer annular plate, and the inner plate is positioned inside the outer annular plate to form a co-axial formation.

18. The method of claim 10, wherein the interrogation unit comprises a tubular structure, wherein the first and second plates are secured on an inner surface of the tubular structure, and wherein the tubular structure is configured to allow the ingestible device to pass through inside the tubular structure.

* * * * *